(12) United States Patent
Kramp

(10) Patent No.: US 7,379,532 B2
(45) Date of Patent: May 27, 2008

(54) ECG-BASED ROTATIONAL ANGIOGRAPHY FOR CARDIOLOGY

(75) Inventor: George Kramp, Elmhurst, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 18 days.

(21) Appl. No.: 11/545,250

(22) Filed: Oct. 10, 2006

(65) Prior Publication Data

US 2008/0031417 A1 Feb. 7, 2008

Related U.S. Application Data

(60) Provisional application No. 60/834,725, filed on Aug. 1, 2006.

(51) Int. Cl.
*H05G 1/44* (2006.01)

(52) U.S. Cl. ............... 378/108; 378/197; 600/428

(58) Field of Classification Search ............ 378/4, 378/8, 19, 95, 108, 193–198; 600/425, 427, 600/428

See application file for complete search history.

(56) References Cited

U.S. PATENT DOCUMENTS 6,324,254 B1 * 11/2001 Pflaum .............. 378/95

6,507,639 B1 * 1/2003 Popescu .............. 378/108

\* cited by examiner

*Primary Examiner*—Courtney Thomas
(74) *Attorney, Agent, or Firm*—Peter Kendall

(57) ABSTRACT

A C-arm X-ray system includes synchronized ECG gating for enhanced cardiac soft-tissue imaging. The system includes an X-ray source disposed on a C-arm for rotation in a circular path about a patient and configured to release X-ray radiation synchronously with an ECG-gating signal, an X-ray image sensor disposed on the C-arm in a fixed opposing position to the X-ray source and configured to rotate with the source and receive the X-ray radiation and an ECG unit for acquiring ECG data from the patient. The system also includes a digital image acquisition processor arranged in communication with the X-ray source, X-ray image sensor and ECG unit for acquiring 2D projection images at predetermined C-arm angulations in the presence of the ECG-gating signal and an image processor arranged in communication with the digital image acquisition processor to receive and process the series of 2D projection images and reconstruct a continuous 3D volumetric image of the patient's cardiac soft tissue therefrom. A user interface to allow user control of the C-arm system and to display the continuous 3D volumetric image.

20 Claims, 4 Drawing Sheets

US 7,379,532 B2

ECG-BASED ROTATIONAL ANGIOGRAPHY FOR CARDIOLOGY

PRIORITY CLAIM TO RELATED APPLICATION

This application claims priority from U.S. Provisional Patent Application Ser. No. 60/834,725, filed Aug. 1, 2006, the disclosure of which is incorporated by reference in its entirety herein.

BACKGROUND OF THE INVENTION

1. Field of the Invention

The present invention relates to 3D rotational angiography (3D RA), and more particularly relates to synchronized 3D rotational angiographic systems and processes for enhanced soft tissue imaging with optimized for X-ray dose reduction and improved patient throughput.

2. Description of the Related Art

Angiography refers generally to the capture and representation of blood vessels, in particular, the arteries and veins of the human body by means of X-ray imaging. 3D rotational angiography (3D RA) includes acquiring a series of 2D X-ray projection images (raw images) recorded at different projection angles, and using a sub-set of the series of raw images to generate a 3D RA image data record of the blood vessels to be examined. 3D RA may be implemented on an X-ray system including a rotational C-arm to acquire the series of projection images along a circular orbit while a continuous injection of contrast agent (contrast bolus) is administered into the vasculature of the patient under examination. The conventional C-arm X-ray system includes an X-ray source and X-ray sensor or detector (or image intensifier (XRII) camera) that is mounted on the C-arm in an opposing position with respect to the source, for acquiring the 2D projection images. A 3D reconstruction processor receives the series of 2D projection (raw) images and implements a process such as cone beam reconstruction to generate a 3D reconstruction of the vasculature under study.

Typically, the 3D reconstructed images or angiogram are studied by clinician(s) to support interventional procedures, e.g., an endovascular procedure such as percutaneous transluminal coronary angioplasty. During the endovascular procedure, 2D fluoroscopy is carried out with the same X-ray C-arm system used for the 3D angiographic procedure, preferably with the 3D reconstruction available for viewing on a split screen or a second monitor. The 2D fluoroscopy also includes "roadmapping," which is 2D fluoroscopic imaging and supports navigation and maneuvering of the catheters through the patient's vasculature. In a roadmapping procedure, a contrast-enhanced fluoroscopic image is captured and stored, and that image is subtracted from subsequent images. The result is a static display of the vascular structures, typically displayed in white, while the catheter appears in black. The roadmapping, however, may display positional ambiguity. To remedy such positional ambiguity, the clinician must inject a contrast agent into the vasculature to opacify the vessels.

In cardiac angiography, where the heart and its coronary arteries are under study, it is problematic for recording purposes that the blood vessels are subject to constant movement as a result of the heartbeat rhythm. ECG gating is known for use in 3D RA imaging of the ventricles and coronary arteries, and arteries proximate the heart. For example, Onno Wink, et al., Coronary Intervention Planning Using Hybrid 3D Reconstruction, MICCAI 2002, LNCS 2488, pgs. 604-611 (Springer Verlag 2002) discloses a 3D RA process where 2D raw images are synchronized with the cardiac rhythm using an ECG signal such that only the 2D projection (raw) images recorded during a low-movement phase of the cardiac cycle are used to reconstruct the 3D image data. U.S. Pat. No. 6,404,850, to Heinz Horbaschek, discloses a cardioangiography apparatus that carries out 3D RA and provides compensation for cardiac motion with a cardiac motion compensation unit, narrowing the imaging to a small volume that includes a region of interest, e.g., a stenosis.

Such conventional systems and techniques, however, tend to realize only a small amount of useable images taken during the 2d projection or fluoroscopic imaging. The X-ray source or emitter, however, typically exposes the patient to x-rays, continuously, or at least for all useable and non-useable 2D projection or raw images that are acquired. More particularly, during conventional ECG gating-based fluoroscopy, only a few raw 2D projection images may be used from the generally several hundred raw images recorded during a full rotation of the X-ray emitter (source) and detector unit (X-ray sensor). Not only is the patient (and clinician) exposed for each unusable 2D projection image (regardless of whether operating in continuous or pulsed mode), but also the reduction in the number of useable images from a set or scene can result in significant deterioration of the quality of the reconstructed 3D image with respect to spatial and contrast resolution.

In order to overcome such shortcomings of the prior art, an inventive 3D C-arm X-ray system for 3D RA, and processes for using the system are disclosed and described herein to provide for optimal dose reduction, accurate 3D reconstruction of the heart's chambers and/or coronary vasculature and faster patient throughput when utilized with an ECG triggering and corresponding acquisition of 2D raw projection images of same.

DESCRIPTION OF DRAWING FIGURES

FIG. 2b is a plot of the patient's ECG signal upon which is superimposed rotation-based timing of 2D projections of FIG. 2a;

DETAILED DESCRIPTION OF THE EXEMPLARY EMBODIMENTS

Figure 1:
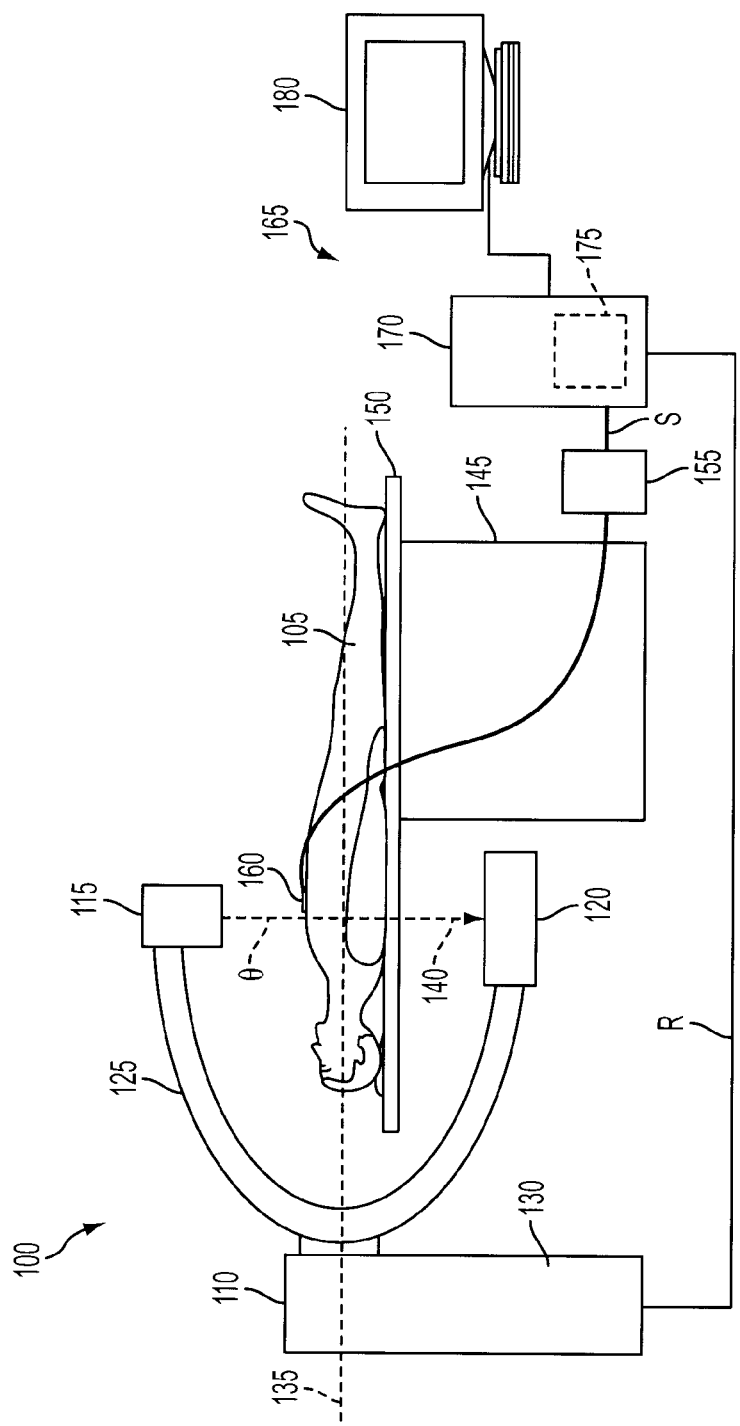
FIG. 1 is a schematic diagram of a C-arm X-ray system for 3D rotational angiography of the invention.

FIG. 1 is a schematic diagram of an inventive C-arm system 100 for 3D rotational angiographic (3D RA) imaging of a chest area of a patient 105, e.g., 3D imaging the cardiac vasculature and chambers. The C-arm X-ray system ("system") is designed for optimal X-ray dose reduction during fluoroscopic acquisition of a series of 2D raw projection images, improved heart chamber imaging and faster patient throughput when implemented with the inventive ECG triggering. System 100 includes a recording unit 110, comprising an X-ray emitter 115 and X-ray detector 120. The X-ray emitter 115 and detector 120 are disposed opposite each other as mounted at the ends of a C-arm 125. The C-arm 125 is supported roughly in its center on a stand 130, in order that the C-arm rotates about its isocentric axis 135. The C-arm construction provides that a central beam 140 of X-ray radiation may be swung or directed at any projection angle (θ) in relation to the surrounding space within a recording plane perpendicular to the isocentric axis 135.

System 100 further includes a patient table 145 with tabletop 150, which are together inserted into an opening in C-arm 125 between the X-ray emitter and detector. An ECG unit 155 is shown in the figure with a number of ECG sensors 160 (attached to patient 105), and a control and evaluation unit 165. The control and evaluation unit 165 includes a data processing unit 170 in which an evaluation unit 175 is used to generate the 3D image data record (i.e., the 3D RA image). The control and evaluation unit 165 includes input/output means 180, e.g., a screen, keyboard, mouse, etc., for inputting control instructions for displaying status variables, examination results, etc. During an examination, the recording unit 110 provides raw 2D projection image data to the evaluation unit 240 at each angular rotation (or "stop") of the C-arm only when the ECG unit provides a radiation control signal to the evaluation unit.

Accordingly, the emitter irradiates the patient once at each angulation stop to realize a 2D projection image (at angle θ) at an exact desired point in the ECG detected cardiac cycle. In other words, at each C-arm stop or event, there is no irradiation until the radiation control signal, time-correlated to a fixed point in the patient's cardiac cycle is generated using the ECG data. The desired cardiac phase is either user programmed, or it may be calculated automatically by the system.

Figure 2A:
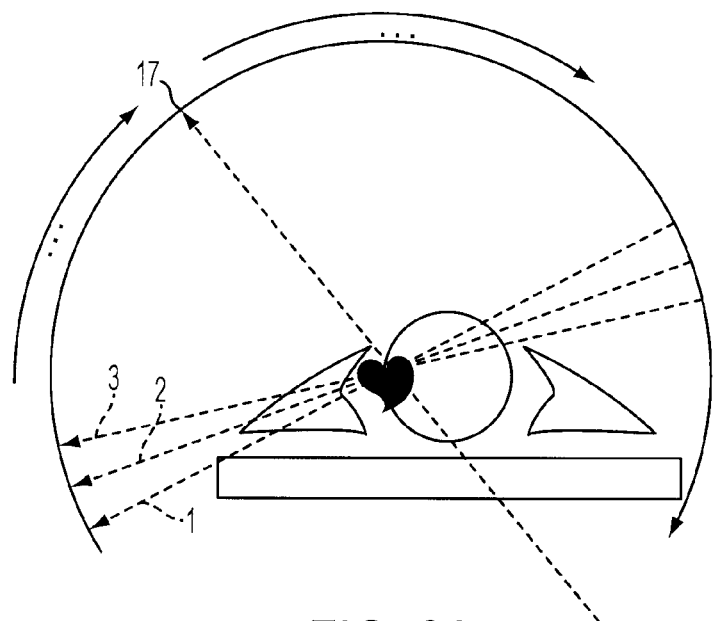
FIG. 2a illustrates projection angles through a patient's heart using a conventional C-arm X-ray system and process.
Figure 2B:
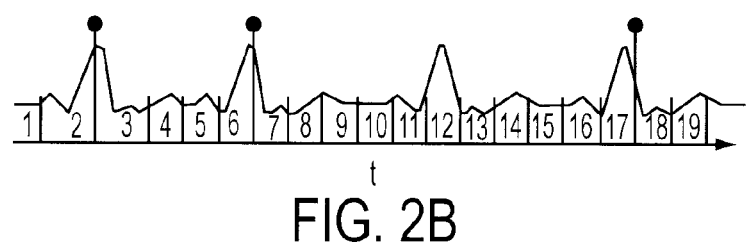

To further the improvement realized by the inventive ECG gating, FIG. 2a illustrates conventional C-arm operation for cardiac imaging a patient 105 positioned on a table 150. The conventional C-arm X-ray system (not shown in FIG. 2a) steps through its angular rotations to generate a series of N raw 2D projection images. FIG. 2b is a plot of the patient's ECG signals upon which the timing of each of the N stops, corresponding to the N raw 2D projection images upon which the timing is superimposed. The conventional pulsed irradiation and raw 2D projection images it generates are not acquired synchronously with the patient's electrical characteristics; the irradiation is merely angle-based (angular rotation). As can be seen in FIG. 2b, images 2 and 6 could be utilized from the scene or series of 2D raw projection images because these appear to correlate to the patient's R-wave. Image 17 of the acquired set or scene could be of use with respect to the R-wave periodicity, but as should be apparent to the skilled artisan, image 17 does not correlate exactly, or substantially exactly to the R-wave peak.

Typically, a clinician or radiologist who wishes to view or analyze the R-wave acquired cardiac images based on the ECG signals must manually extract the ECG-related images. Not only is such manual viewing and extraction of images associated with a fixed portion of the cardiac cycle lengthy and cumbersome, but also the patient (and possibly the clinician) may be exposed to unnecessary radiation. The non-R-wave related raw 2D projections are of little use when R-wave images are to be focused upon (in a particular study) using conventional hardware and methods.

In order to approve the state of the art, the C-arm system for ECG-gated 3D RA of the cardiac chambers and vasculature of this invention controls the release of X-rays from the X-ray source, at each angular stop, until the same time or substantially the same time in the patient's cardiac cycle. In particular, the inventive C-arm X-ray system 100 of FIG. 1 is designed so that the start and stop angles (θ) for a 3D RA study are defined, or fixed so that the X-ray emitter does not irradiate until the patient's heart is at the same periodic portion of his/her cardiac cycle at each stop. The inventive system 100 may be user-programmed to define the rotational step size between each acquired image, and to define the fixed phase at which the irradiation occurs to realize a desired resolution of the 3D reconstructed image for various 3D RA imaging applications and procedures.

Figure 3A:
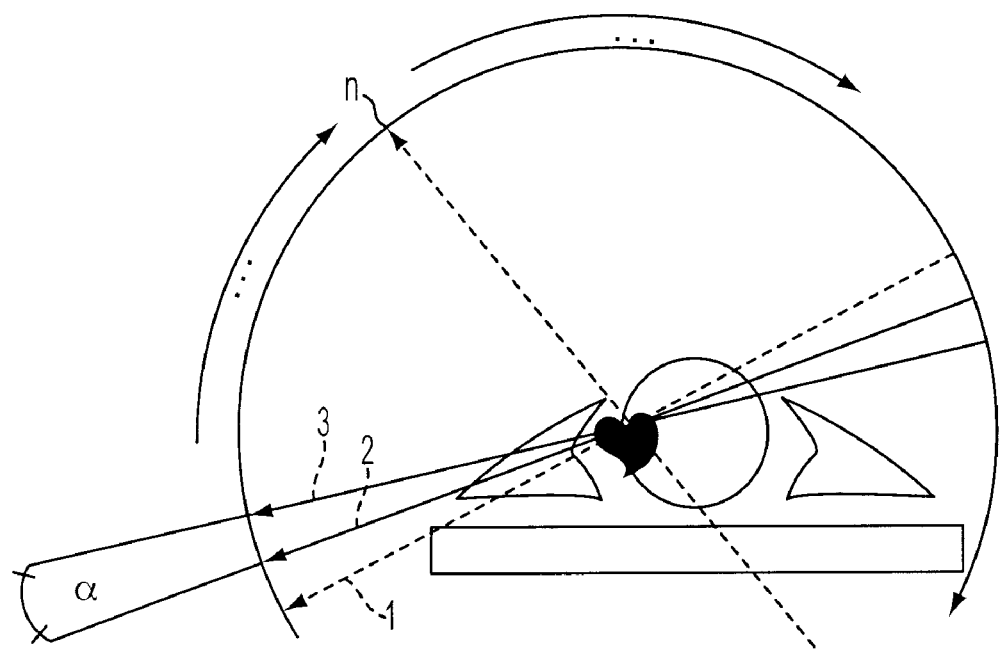
FIG. 3a illustrates projection angles defined to image a patient's cardiac anatomy by an inventive C-arm X-ray system with ECG gating in accordance with an embodiment of the invention.
Figure 3B:
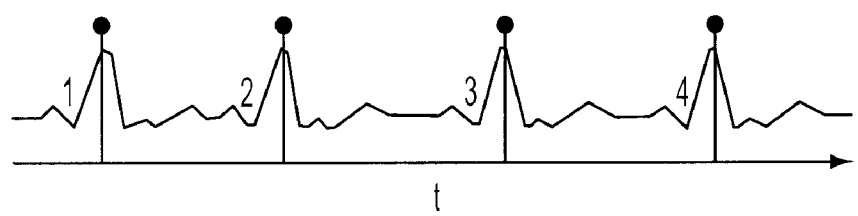
FIG. 3b is plot of the patient's ECG signals upon which is superimposed the ECG gated signals which control the irradiation at each stop of a C-arm X-ray system in accordance with an embodiment of the invention.

FIG. 3a is an illustration of projection angles of X-ray irradiation irradiating a patient's (105) cardiac anatomy while positioned on a table 150. FIG. 3b is a plot of the patient's ECG signals superimposed on a scene or series of raw 2D projection images derived by the inventive system 100. Operational parameters may be defined manually by patient input, or automatically calculated by the system 100. In the example depicted in FIGS. 3a and 3b, the step angulation is set to 7.5 degrees and the radiation control signal is arranged so that a series of 64 images is acquired at 64 r-wave occurrences. In operation, the C-arm begins the image acquisition at the start position. Upon the first R-wave occurrence at the start position (based on the ECG signal), the X-ray irradiation is released by the X-ray source to acquire the first R-wave 2D projection image. Immediately following the acquisition of the first 2D raw projection image at the start position, the C-arm is rotated to the next angle or rotation step, where it "waits" for the next R-wave event before taking the next 2D raw projection image. X-ray exposure is accordingly reduced for both the patient and clinician, and the clinician is no longer required to manually select the images, improving workflow.

Figure 4:
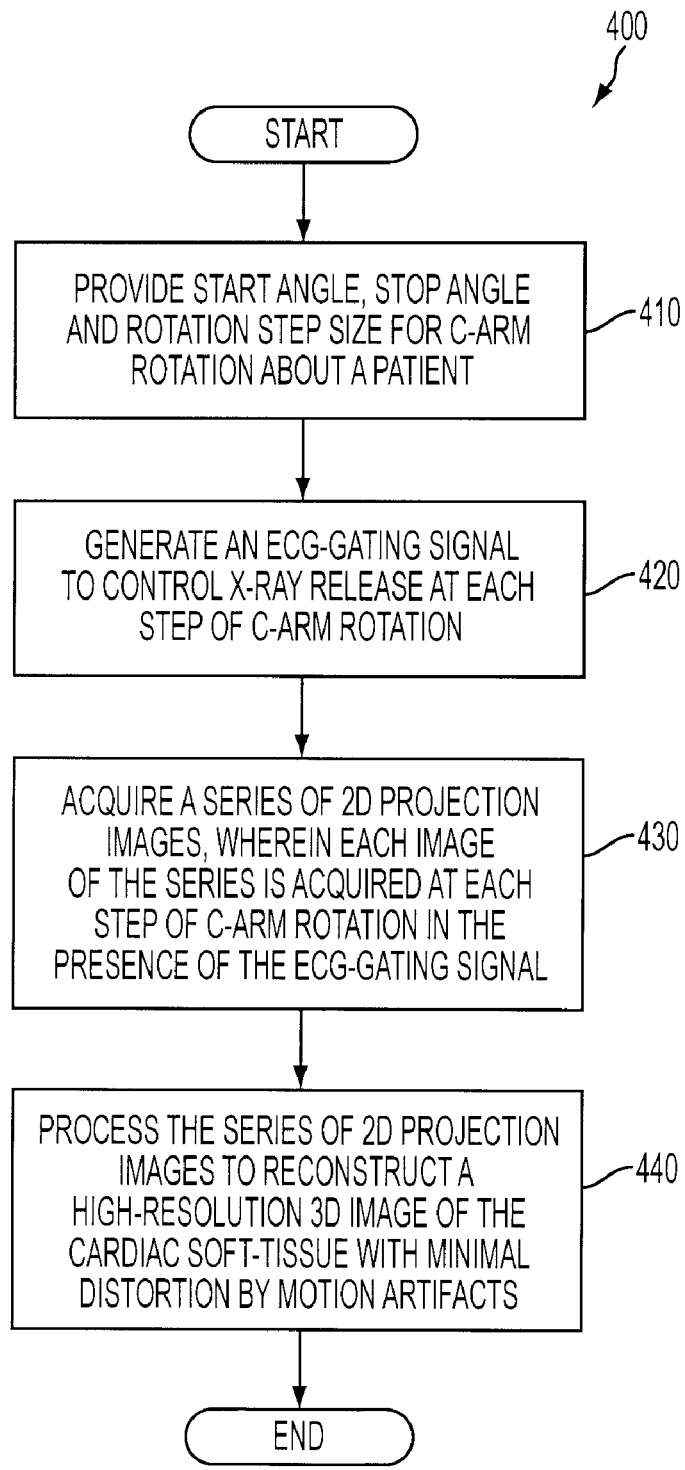
FIG. 4 is a schematic flow diagram of an invention 3D RA method utilizing ECG gating in accordance with an embodiment of the invention.

FIG. 4 is a schematic flow diagram, which defines one embodiment of an inventive method 400 of the invention. The inventive method may be included in a "dynavision" operation, wherein a dynavision exposure series is acquired from a patient at rest on a table, as shown in FIG. 1. The method is ECG-synchronized, and implemented for 3D rotational angiographic (3D RA) imaging of a patient's cardiac anatomy using a C-arm X-ray system. Upon initiation of the method, a step represented by block 410 includes providing a start angle, a stop angle and a rotation step size for C-arm rotation about the patient. These inputs may be automatically generated by a processor included in the C-arm X-ray system, or input by a user through a user interface.

Block 420 represents a step of generating an ECG-gating signal to control X-ray release at each step of C-arm rotation. The ECG gating signal may be generated directly within an ECG unit, or generated by a processor automatically. The user chooses a phase of the patient's cardiac phase, for example, the R-wave. Block 430 represents a step of acquiring a series of 2D projection images. Each or the acquired 2D projection images of the series is acquired at each step of C-arm rotation in the presence of the ECG-gating signal. That is, at each step in c-arm rotation, a 2D projection image (raw image) is acquired synchronously with the ECG gating signal, whereby one image may be acquired at the same cardiac phase at each rotational step, to minimize x-ray exposure and movement-associated image artifacts when two or more of the acquired series are used to generate a real-time 3D RA image.

Block 440 represents a step of processing the series of 2D projection images to reconstruct a high-resolution 3D image of the cardiac soft-tissue. The inventive method may include preceding the image acquisition step by a safety test run. For that matter, the method may further implement real-time subtraction imaging, roadmapping and interventional 2D fluoroscopy.

While the present invention has been shown and described with reference to certain embodiments thereof, it will be understood by those skilled in the art that various changes in form and details may be made therein without departing from the spirit and scope of the invention as defined by the appended claims.

The invention claimed is:

1. A C-arm X-ray system with synchronized ECG gating for enhanced cardiac soft-tissue imaging, comprising:
   an X-ray source disposed on a C-arm for rotation in a circular path about a patient and configured to release X-ray radiation periodically and synchronously with an ECG-gating signal that is periodically activated at a fixed point in each cycle of the patient's heart, wherein said periodic synchronous release reduces the patient's accumulated X-ray radiation exposure during said cardiac soft-tissue imaging;
   an X-ray image sensor disposed on the C-arm in a fixed opposing position to the X-ray source and configured to rotate with the source and receive the X-ray radiation;
   an ECG unit for acquiring ECG data from the patient;
   a digital image acquisition processor arranged in communication with the X-ray source, X-ray image sensor and ECG unit for acquiring 2D projection images by the X-ray image sensor at predetermined C-arm angulations at the release of the X-ray radiation synchronously in the presence of the periodic ECG-gating signals;
   an image processor arranged in communication with the digital image acquisition processor to receive and process the series of 2D projection images and reconstruct a continuous 3D volumetric image of the patient's cardiac soft tissue therefrom; and
   a user interface to allow user control of the C-arm X-ray system and to display the continuous 3D volumetric image.

2. The C-arm X-ray system as set forth in claim 1, wherein the ECG-gating signal activates the X-ray source at a regular, fixed phase of the cardiac cycle at each angulation step of the C-arm as it rotates about the circular path.

3. The C-arm X-ray system as set forth in claim 1, wherein the ECG-gated signal is generated automatically in the digital image acquisition subsystem.

4. The C-arm X-ray system as set forth in claim 3, wherein the angulations are defined automatically by the system, or by user input via the user interface.

5. The C-arm X-ray system as set forth in claim 4, wherein a size of the angulations qualifies image resolution.

6. The C-arm X-ray system as set forth in claim 1, wherein the C-arm is mounted on a floor or a ceiling.

7. The C-arm X-ray system as set forth in claim 1, wherein the C-arm is a mobile C-arm.

8. The C-arm X-ray system as set forth in claim 1, wherein the c-arm further includes a collimator to reduce X-ray scatter.

9. The C-arm system as set forth in claim 1, further comprising a workstation, wherein the work station includes the image processor and presents the user interface, and which allows the X-ray system user to perform calibrations and measurements including identifying cardiac vasculature and anomalies if present therein.

10. The C-arm system as set forth in claim 1, wherein the X-ray image detector is a flat rectangular or flat quadratic semiconductor detector.

11. The C-arm X-ray system as set forth in claim 10, wherein the X-ray image detector comprises a live imaging control mechanism that supports digital spot imaging.

12. The C-arm X-ray system as set forth in claim 1, wherein the acquisition and image processors support digital subtraction angiography (DSA).

13. The C-arm X-ray system as set forth in claim 1, further comprising a second X-ray emitter, and a second X-ray detector, wherein the first and second detectors and first and second emitters operate as a dual plane system.

14. A method for ECG-synchronized 3D rotational angiographic (3D RA) imaging a patient's cardiac anatomy using a C-arm X-ray system including a C-arm with opposing ends at which are respectively disposed an X-ray source and an X-ray receiver, the method comprising the steps of:
   providing a user interface to interact with a system user to define a start angle, a stop angle, a rotation step size for C-arm rotation about the patient, and a fixed point in the patient's cardiac cycle to release X-ray radiation;
   generating an ECG-gating signal at said fixed point, once in each cardiac cycle to control X-ray release periodically at each step of C-arm rotation;
   periodically rotating the C-arm about the patient in rotational steps, and releasing X-ray radiation at each step synchronously with said ECG-gating signal;
   acquiring a series of 2D projection images, wherein each image of the series is acquired at each step of C-arm rotation synchronously with the release of X-ray radiation with said ECG-gating signal;
   processing the series of 2D projection images to reconstruct a high-resolution 3D image of the cardiac soft-tissue with minimal distortion by motion artifacts; and
   presenting the high-resolution 3-D image of the cardiac soft-tissue in a display image using the user interface;
   wherein said periodic synchronous release reduces the patient's accumulated X-ray radiation exposure during said 3D RA imaging.

15. The method as set forth in claim 14, wherein the step of providing includes automatically generating the rotation step size.

16. The method as set forth in claim 14, wherein the step of providing includes that the fixed point in the cardiac cycle correlates to the patient's R-wave, and step of generating generates the ECG-gating signal at R-wave detection.

17. The method as set forth in claim 14, wherein the step of acquiring includes rotating the C-arm after each ECG-controlled 2D projection image acquisition, to move the C-arm to the next step in the rotation, and waiting before a next acquisition until a fixed phase of the cardiac cycle, which defines the ECG-gating signal.

18. The method as set forth in claim 14, wherein the step of acquiring is preceded by a safety test run.

19. The method as set forth in claim 14, wherein the processor carries out real-time subtraction imaging.

20. A computer readable storage medium in which is stored a set of computer readable instructions for use by a processor included in a C-arm X-ray system to implement the method as set forth in claim 14.

* * * * *